(12) United States Patent
Lee et al.

(10) Patent No.: US 11,814,672 B2
(45) Date of Patent: Nov. 14, 2023

(54) COMPLEX OF LNA PROBE AND GRAPHENE OXIDE AND NUCLEIC ACID DETECTION METHOD USING SAME

(71) Applicant: Korea Research Institute of Chemical Technology, Daejeon (KR)

(72) Inventors: Jieon Lee, Daejeon (KR); Woo-keun Kim, Daejeon (KR); Seokjoo Yoon, Daejeon (KR); Bomi Shin, Daejeon (KR)

(73) Assignee: Korea Research Institute of Chemical Technology, Daejeon (KR)

(*) Notice: Subject to any disclaimer, the term of this patent is extended or adjusted under 35 U.S.C. 154(b) by 279 days.

(21) Appl. No.: 17/006,889

(22) Filed: Aug. 30, 2020

(65) Prior Publication Data

US 2021/0324471 A1 Oct. 21, 2021

(30) Foreign Application Priority Data

Apr. 17, 2020 (KR) .......................... 10-2020-0047039

(51) Int. Cl.
*C12Q 1/6813* (2018.01)
(52) U.S. Cl.
CPC ...... *C12Q 1/6813* (2013.01); *C12Q 2531/119* (2013.01); *C12Q 2537/137* (2013.01); *C12Q 2537/1373* (2013.01); *C12Q 2600/178* (2013.01)

(58) Field of Classification Search
None
See application file for complete search history.

(56) References Cited

U.S. PATENT DOCUMENTS

2016/0138096 A1* 5/2016 Min ..................... C12Q 1/6823
506/18

FOREIGN PATENT DOCUMENTS

KR 10-1818177 A 1/2018

OTHER PUBLICATIONS

Huang et al. Small. 2012. 8(7): 977-983 (Year: 2012).*
Piao et al. Appl. Mater. Interfaces. 2012. 4: 6785-6789) (Year: 2012).*

(Continued)

*Primary Examiner* — Carla J Myers
(74) *Attorney, Agent, or Firm* — Klarquist Sparkman, LLP

(57) ABSTRACT

The present invention provides a complex of LNA probe and graphene oxide, and a nucleic acid detection method using the same. In the present invention, LNA-containing molecular beacon is conjugated through covalent bonding with graphene oxide, a single strand of the molecular beacon binds to a target nucleic acid to form a complex, and the complex is separated from graphene oxide to induce a fluorescence signal. The molecular beacon and graphene oxide can be covalently bonded to minimize non-specific signals, and a LNA-added molecular beacon is designed in a double strand to detect a very low concentration of target nucleic acid with high sensitivity, as well as a fluorescent signal, and the multiple target nucleic acids can be detected simultaneously through diversification of the fluorescent signal to enable easy and accurate detection of a nucleic acid biomarker whose specific expression level is specifically changed according to diseases and disease progression.

11 Claims, 17 Drawing Sheets

Specification includes a Sequence Listing.

(56) References Cited

OTHER PUBLICATIONS

Huang et al. Anal. Chem. 2012. 84: 4192-4198 and Supporting Information S1-S8 (Year: 2012).*
Jieon Lee et al., Graphene oxide-based NET strategy for enhanced colorimetric sensing of miRNA. Sensors & Actuators: B. Chemical, 2019, Nov. 28, 2018, pp. 861-867, vol. 282, Elsevier.
Zhen et al., "An Enzyme-Free DNA Circuit-Assisted Graphene Oxide Enhanced Fluorescence Anisotropy Assay for MicroRNA Detection with Improved Sensitivity and Selectivity", Analytical Chemistry, Jul. 24, 2017, pp. 8766-8771, vol. 89 No. 17.
Adegoke et al., "The use of nanocrystal quantum dot as fluorophore reporters in molecular beacon-based assays", Nano Convergence, Dec. 1, 2016, pp. 1-13, vol. 3 No. 32.
Shin et al., "Duplex DNA-functionalized graphene oxide: A versatile platform for miRNA sensing," *Sensors and Actuators B: Chemical*, vol. 305, 127471, 7 pages with additional 7 pages of Supporting Information, 2020.

* cited by examiner

Duplex molecular beacon containing LNA for miR-21 (LMB-21) on GO :

(Upper)    5'-            TCA GAC TGA TGT TGA – NH – GO (3')
                Toehold   ••• ••• ••• ••• •••
(F-Bottom) 3'- A TCG AAT  AGT CTG ACT ACA ACT – FAM – 5' miR-21     5'– U AGC UUA UCA GAC UGA UGU UGA –3'

SEQUENCE LISTING

<160> NUMBER OF SEQ ID NOS: 11

<210> SEQ ID NO 1
<211> LENGTH: 22
<212> TYPE: RNA
<213> ORGANISM: Artificial Sequence
<220> FEATURE:
<223> OTHER INFORMATION: miR-21

<400> SEQUENCE: 1
uagcuuauca gacugauguu ga						22

<210> SEQ ID NO 2
<211> LENGTH: 15
<212> TYPE: DNA
<213> ORGANISM: Artificial Sequence
<220> FEATURE:
<223> OTHER INFORMATION: LMB-21 upper strand

<400> SEQUENCE: 2
tcagactgat gttga						15

<210> SEQ ID NO 3
<211> LENGTH: 22
<212> TYPE: DNA
<213> ORGANISM: Artificial Sequence
<220> FEATURE:
<223> OTHER INFORMATION: LMB-21 bottom strand

<400> SEQUENCE: 3
tcaacatcag tctgataagc ta						22

<210> SEQ ID NO 4
<211> LENGTH: 22
<212> TYPE: RNA
<213> ORGANISM: Artificial Sequence
<220> FEATURE:
<223> OTHER INFORMATION: miR-125b

<400> SEQUENCE: 4
ucccugagac ccuaacuugu ga						22

<210> SEQ ID NO 5
<211> LENGTH: 22
<212> TYPE: RNA
<213> ORGANISM: Artificial Sequence
<220> FEATURE:
<223> OTHER INFORMATION: let-7a

<400> SEQUENCE: 5
ugagguagua gguuguauag uu						22

<210> SEQ ID NO 6
<211> LENGTH: 22
<212> TYPE: RNA
<213> ORGANISM: Artificial Sequence
<220> FEATURE:
<223> OTHER INFORMATION: miR-122

<400> SEQUENCE: 6
uggaguguga caaugguguu ug						22

<210> SEQ ID NO 7
<211> LENGTH: 27
<212> TYPE: RNA
<213> ORGANISM: Artificial Sequence

```
<220> FEATURE:
<223> OTHER INFORMATION: scRNA

<400> SEQUENCE: 7
gcaucgagcu gaagggcauc gacuuca                                          27

<210> SEQ ID NO 8
<211> LENGTH: 15
<212> TYPE: DNA
<213> ORGANISM: Artificial Sequence
<220> FEATURE:
<223> OTHER INFORMATION: LMB-125b upper strand

<400> SEQUENCE: 8
gaccctaact tgtga                                                       15

<210> SEQ ID NO 9
<211> LENGTH: 22
<212> TYPE: DNA
<213> ORGANISM: Artificial Sequence
<220> FEATURE:
<223> OTHER INFORMATION: LMB-125b bottom strand

<400> SEQUENCE: 9
tcacaagtta gggtctcagg ga                                               22

<210> SEQ ID NO 10
<211> LENGTH: 15
<212> TYPE: DNA
<213> ORGANISM: Artificial Sequence
<220> FEATURE:
<223> OTHER INFORMATION: LMB-let 7a upper strand

<400> SEQUENCE: 10
gtaggttgta tagtt                                                       15

<210> SEQ ID NO 11
<211> LENGTH: 22
<212> TYPE: DNA
<213> ORGANISM: Artificial Sequence
<220> FEATURE:
<223> OTHER INFORMATION: LMB-let 7a bottom strand

<400> SEQUENCE: 11
acctatacaa cctactacct ca                                               22
```

COMPLEX OF LNA PROBE AND GRAPHENE OXIDE AND NUCLEIC ACID DETECTION METHOD USING SAME

CROSS-REFERENCES TO RELATED APPLICATION

This patent application claims the benefit of priority under 35 U.S.C. § 119 from Korean Patent Application No. 10-2020-0047039, filed Apr. 17, 2020, the contents of which are incorporated herein by reference.

BACKGROUND OF THE INVENTION

Field of the Invention

The present invention relates to a complex of LNA probe and graphene oxide, and a nucleic acid detection method using the same.

Description of the Related Art

MicroRNAs (miRNAs) are 17-25 nucleotides non-coding RNAs involved in RNA silencing and post-transcriptional regulation of gene expression. Numerous studies have confirmed that miRNAs play critical roles in diverse biological processes such as cell proliferation, differentiation, angiogenesis, and apoptosis. Their abnormal expression is associated with a variety of serious diseases such as cancer, viral infections, immune diseases and neurodegenerative disorders. For example, miRNA-21, which is known to have oncogenic functions, is constantly overexpressed in various types of malignant tumors such as breast cancer, pancreatic cancer, and hepatocellular carcinoma. In 2008, some tumor-derived miRNAs with high stability were found in serum and plasma of cancer xenograft mice. Tumor-specific miRNAs are also detected in patients' clinical samples, and thus miRNAs are attracting attention as promising non-invasive biomarkers.

In general, real-time PCR and miRNA microarray have been conventionally used for quantitative detection of miRNA. However, due to complicated procedures and expensive reagents and devices, there were limitations in actual clinical applications. In order to solve the above problems, there have been many technical and scientific attempts to construct a simple and fast detection platform. Many miRNA detection systems based on various techniques combining fluorescent, colorimetric, surface plasmon resonance and electrochemical methods and sophisticated signal amplification methods have been proposed in recent decades. Among them, nanomaterial-based miRNA detection and analysis methods have been developed with considerable attention.

Thus, the present inventors developed a versatile and practical platform for miRNA detection using a graphene oxide (GO)-DNA conjugate. Graphene oxide is an inexpensive nanomaterial that can be synthesized in large quantities. It has both hydrophilic and hydrophobic parts, and is used in various biosensor applications because it maintains the properties of high thermal conductivity and electrical conductivity. Particularly, graphene oxide has been extensively used for the development of fluorescent nucleic acid sensing systems, which rely on the efficient fluorescent quenching capability and high probe-loading capacity of GO. In biosensors, graphene oxide generally exhibits strong affinity to single-stranded nucleic acids (ssNAs) through pi-pi stacking or hydrogen bonding interactions, and thus serves as a material for high-efficiency separation of ssNAs. However, the complex exhibits such problems as inducing non-specific signals by reacting with various competitive biomolecules such as proteins, nucleic acids and fats.

To solve those problems, the present inventors, while trying to develop a new target nucleic acid detection system, have developed a target nucleic acid detection system using LNA (locked nucleic acid)-containing molecular beacon and graphene oxide based on the TMSD (toehold-mediated strand displacement) principle.

TMSD is a molecular tool that exchanges one strand of DNA or RNA for another strand without the aid of an enzyme, which is based on hybridization of two complementary strands of DNA or RNA through Watson-Crick base pairs (AT/U and C-G), and uses a process called branch migration. TMSD begins with a double-stranded DNA complex consisting of an original strand and a protective strand. The original strand has a so-called "toehold" protruding region, which is complementary to the third DNA or RNA strand called the invading strand. The toehold region of the original strand hybridizes with the complementary invading strand to form a complex composed of three nucleic acid strands to proceed with the TMSD process. As a result, the original strand and the invading strand are combined to form a double strand, and the protective strand originally bound to the original strand is separated.

LNA is an RNA analog, and the ribose ring is "locked", making it an ideal structure for Watson-Crick pairing. LNA nucleotides have a higher binding force to complementary strands than the conventional DNA or RNA nucleotides, and as a result, they have stability even at high temperatures when binding to complementary strands. Therefore, LNA nucleotides show high sensitivity and specificity, and are easy to detect single base differences.

Based on this, the present inventors confirmed that a complex was formed by binding a single strand of LNA-containing molecular beacon with a target nucleic acid using LNA-containing molecular beacon and graphene oxide, the complex was separated from graphene oxide to induce a fluorescence signal, a very low concentration of the target nucleic acid could be detected with high sensitivity, and the multiple target nucleic acids could be detected simultaneously through diversification of the fluorescent signal, resulting in the completion of the present invention.

SUMMARY OF THE INVENTION

It is an object of the present invention to provide a composition for detecting nucleic acid capable of detecting a target nucleic acid with high sensitivity by recognizing a low concentration of the target nucleic acid using LNA (locked nucleic acid), and simultaneously detecting multiple target nucleic acids through wavelength diversification of a fluorescent signal.

It is another object of the present invention to provide a nucleic acid detection method using the composition.

To achieve the above objects, the present invention provides a composition for detecting nucleic acid comprising LNA-containing molecular beacon and graphene oxide, wherein the molecular beacon is formed by complementarily conjugating the first single strand containing the target nucleic acid binding sequence and the second single strand bound with graphene oxide at least in part, and the first single strand is separated from the second single strand and bound to the target nucleic acid in the presence of the target nucleic acid.

The present invention also provides a nucleic acid detection method comprising the following steps:

covalently conjugating LNA-containing molecular beacon and graphene oxide;

obtaining a mixture by mixing the composition for detecting nucleic acid obtained in above step and a sample containing the target nucleic acid; and detecting the target nucleic acid in the mixture.

In addition, the present invention provides a kit for detecting nucleic acid comprising LNA-containing molecular beacon and graphene oxide, wherein the molecular beacon is formed by complementarily conjugating the first single strand containing the target nucleic acid binding sequence and the second single strand bound with graphene oxide at least in part, and the first single strand is separated from the second single strand and bound to the target nucleic acid in the presence of the target nucleic acid.

Advantageous Effect

According to the composition, kit and method for detecting nucleic acid of the present invention, LNA-containing molecular beacon is conjugated through covalent bonding with graphene oxide, and a single strand of the molecular beacon binds to a target nucleic acid to form a complex, and the complex is separated from graphene oxide to induce a fluorescence signal. The molecular beacon and graphene oxide can be covalently bonded to minimize non-specific signals, and a LNA-added molecular beacon is designed in a double strand to detect a very low concentration of target nucleic acid with high sensitivity, as well as a fluorescent signal, and the multiple target nucleic acids can be detected simultaneously through diversification of the fluorescent signal. Through the present invention, it is possible to easily and accurately detect a nucleic acid biomarker whose specific expression level is specifically changed according to toxic diseases and disease progression.

BRIEF DESCRIPTION OF THE DRAWINGS

FIG. 4A is a diagram showing the signal strength of gel electrophoresis according to the concentration of the target (miR-21) when GO-LMB is included compared to the control group without GO-LMB.

FIG. 4B is a graph showing that the signal strength of gel electrophoresis is increased in proportion to the concentration of the target (miR-21).

FIG. 5A is a graph showing the intensity of the fluorescent signal over time by varying the concentration of the target (miR-21).

FIG. 5B is a graph showing the intensity of the fluorescent signal according to the concentration of the target (miR-21) by wavelength.

FIG. 5C is a graph showing the degree of improvement in the intensity of the fluorescent signal for each miRNA.

FIG. 5D is a graph showing the degree of improvement in the intensity of the fluorescent signal for each miRNA by wavelength.

FIG. 6A is a graph showing the degree of improvement in the intensity of the fluorescence signal of GO-LMB according to the concentration of the target (miR-21).

FIG. 6B is a graph showing the degree of improvement in the intensity of the fluorescent signal of GO-MB according to the concentration of the target (miR-21).

FIG. 7A is a graph showing the intensity of the fluorescent signal of GO-LMB-21 and GO-cDNA-21 in the present of miR-21 at the concentration of 0 or 100 nM.

FIG. 7B is a graph showing the intensity of the fluorescent signal of GO-LMB-21 and GO-cDNA-21 according to the concentration of miR-21 and time.

FIG. 7C is a graph showing the intensity of the fluorescent signal of GO-LMB-21 in the present of miR-21 at the concentration of 0 or 100 nM by wavelength.

FIG. 7D is a graph showing the intensity of the fluorescent signal of GO-cDNA-21 in the present of miR-21 at the concentration of 0 or 100 nM by wavelength.

FIG. 8A, FIG. 8B, FIG. 8C, and FIG. 8D is a set of graphs confirming whether GO-LMB -21 shows high sensitivity in cell lysates.

FIG. 8A is a graph showing the F/FO values of GO-LMB-21 and the conventional GO sensor according to the concentration of BSA.

FIG. 8B is a graph showing the intensity of the fluorescence signal according to the concentration of miR-21 in the presence of 100 μg/ml of BSA.

FIG. 8C is a graph showing the intensity of the fluorescence signal according to the concentration of miR-21 in the presence of 100 μg/ml of BSA by wavelength.

FIG. 10A is a graph showing the wavelength at which each target miRNA is simultaneously detected by FIG. 10B is a diagram showing the fluorescent images illustrating that each target miRNA is simultaneously detected by treating GO-LMB-21/125b/7a to various mixtures containing at least one target miRNA at the concentration of 100 nM.

FIG. 10C is a graph showing the intensity of the fluorescence signal illustrating that each target miRNA is simultaneously detected by treating GO-LMB-21/125b/7a to various mixtures containing at least one target miRNA at the concentration of 100 nM.

DETAILED DESCRIPTION OF THE INVENTION

Figures 1, 2:
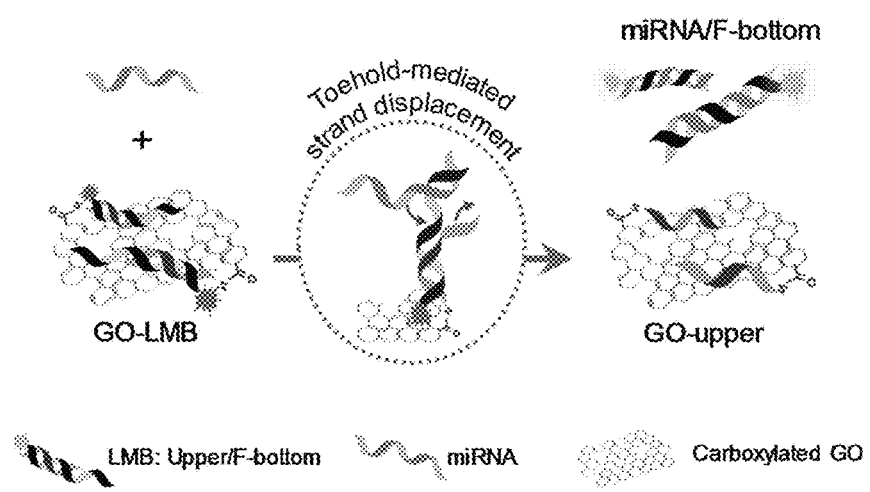
FIG. 1 is a diagram showing the outline of a method for detecting miRNA using a GO-LMB complex.
FIG. 2 is a diagram showing the DNA sequences of the target (miR-21) and molecular beacon (LMB-21) used in the embodiments of the present invention. The DNA sequences correspond to SEQ ID NO: 1 (Upper), SEQ ID NO: 2 (F-Bottom), and SEQ ID NO: 3 (miR-21).

Hereinafter, the present invention is described in detail.

The present invention provides a composition for detecting nucleic acid comprising LNA-containing molecular beacon and graphene oxide, wherein the molecular beacon is formed by complementarily conjugating the first single strand containing the target nucleic acid binding sequence and the second single strand bound with graphene oxide at least in part, and the first single strand is separated from the second single strand and bound to the target nucleic acid in the presence of the target nucleic acid.

Herein, the target nucleotide binding sequence can be understood as a sequence capable of complementarily binding at least a portion of a target nucleotide sequence, and the first single strand binds to the target nucleic acid through the complementary binding of the target nucleic acid binding sequence and the target nucleic acid and is separated from the second single strand.

In addition, the sequence complementary to the target nucleic acid binding sequence refers to a sequence in which at least a part of the target nucleic acid binding sequence of the first single strand can form a complementary binding.

In an aspect of the present invention, the first single strand and the second single strand can independently have a length of 10 to 30 nucleotides, but not always limited thereto.

In addition, at least a part of the first single strand is complementary to at least a part of the second single strand, and can have a duplex of 15 to 25 nucleotides in length, for example.

Furthermore, the target nucleic acid binding sequence of the first single strand is a sequence capable of binding to the target nucleic acid through complementary base pairing, and can be, for example, 20 to 25 nucleotides in length.

In a preferred embodiment of the present invention, the target nucleic acid binding sequence can be designed as a sequence complementary to the target nucleic acid sequence, and some bases can be substituted, deleted, or added within a range that does not affect the binding force with the target nucleic acid.

In an aspect of the present invention, each strand of the LNA-containing molecular beacon (LMB) can be 15 to 30 nucleotides in length, preferably the first single strand can be 15 to 25 nucleotides, and the second single strand can be 10 to 20 nucleotides in length.

In addition, at least a part of the first single strand of the LNA-containing molecular beacon (LMB) can be complementary to at least a part of the second single strand, and the molecule can have a duplex of 10 to 30 nucleotides in length, preferably 15 to 20 nucleotides in length.

Furthermore, the LNA-containing molecular beacon (LMB) can have one or more 3' overhangs including 3' overhangs of the first single strand, and the overhangs can be 5 to 20 nucleotides in length preferably 7 nucleotides in length.

In an aspect of the present invention, it can be understood that the target nucleic acid comprises DNA or RNA having a sequence at least partially complementary to the first single strand of the LNA-containing molecular beacon (LMB). When the target nucleic acid DNA or RNA is present in a sample, the first single strand of the molecular beacon having a complementary sequence is hybridized with the DNA or RNA to become a double-stranded nucleic acid. As this hybrid is dissociated from graphene oxide, the fluorescent substance attached to the first single strand displays a fluorescence signal to detect the target nucleic acid DNA or RNA present in the sample.

Herein, the target nucleic acid DNA can include DNA encoding a protein or DNA not encoding a protein, but not always limited thereto. For example, the said RNA can include mRNA (messenger RNA), tRNA (transfer RNA), rRNA (ribosomal RNA), sRNA (small RNA), snRNA (small nuclear RNA), scRNA (small cytoplasmic RNA), siRNA (small interfering RNA), or miRNA (microRNA), but not always limited thereto. The said RNA can also include RNA translated into protein, RNA not translated into protein, 5'-untranslated region, 3'-untranslated region, or regulatory RNA, but not always limited thereto.

In an aspect of the present invention, the said RNA can include miRNA, but not always limited thereto. The miRNA may be involved in biological functions in vivo, and can include those used as important biomarkers in diagnosis, treatment, or prognosis of various diseases such as breast cancer, lung cancer, liver cancer, pancreatic cancer, stomach cancer, colon cancer, bone cancer, skin cancer, blood cancer, diabetes, or Alzheimer's disease. For example, the miRNA can be involved in lineage specific differentiation in stem cells, but not always limited thereto.

In an aspect of the present invention, the miRNA can include miRNA-21, miRNA-125b, or let 7a, but not always limited thereto. The said miRNA-21, miRNA-125b, or let 7a can be expressed in human cells, but not always limited thereto. The miRNA-21, miRNA-125b, or let 7a can be expressed in breast cancer cells, but not always limited thereto. For example, the miRNA-21, miRNA-125b, or let 7a can be expressed in the breast cancer cell line MDA-MB -231, MDA-MB435 or MCF-7; or in other cancer cells, but not always limited thereto.

In a preferred embodiment of the present invention, the target nucleic acid is miR-21, which can have a sequence of U AGC UUA UCA GAC UGA UGU UGA (SEQ. ID. NO: 1). The first single strand can be 5'-TCA GAC TGA TGT TGA-NH2(3') (SEQ. ID. NO: 2), and the second single strand can be 5'-TCA ACA TCA GTC TGA TAA GCT A-3' (SEQ. ID. NO: 3).

In an aspect of the present invention, the second single strand of the molecular beacon can be covalently conjugated to graphene oxide, and specifically, the amine group of the second single strand of the molecular beacon can be covalently conjugated to the carboxyl group of graphene oxide, but not always limited thereto. The amine group is bound to graphene oxide through covalent conjugation, and can be directed in the same direction as the fluorescent reagent attached to the first single strand.

In an aspect of the present invention, the composition for detecting nucleic acid can attach a fluorescent reagent to the first single strand of the molecular beacon.

For example, the fluorescent reagent can be one or more reagents selected from the group consisting of FAM (6-carboxyfluorescein), Texas red, fluorescein, HEX (2',4',5',7'-tetrachloro-6-carboxy-4,7-dichlorofluorescein), fluorescein chlorotriazinyl, rhodamine green, rhodamine red, tetramethylrhodamine, FITC (fluorescein isothiocyanate), Oregon green, alexafluor, JOE (6-Carboxy-4',5'-Dichloro-2',7'-Dimethoxyfluorescein), ROX (6-Carboxyl-X-Rhodamine), TET (Tetrachloro-Fluorescein), TRITC (tetramethylrodamineisothiocyanate), TAMRA (6-carboxytetramethyl-rhodamine), NED (N-(1-Naphthyl) ethylenediamine), cyanine-based dyes and thiadicarbocyanine. Herein, the fluorescent reagent can be included in the present invention without limitation as long as it can exhibit fluorescence when the first single strand is dissociated from graphene oxide. For example, the fluorescent reagent can include one or more reagents selected from the group consisting of FAM, Cy5 and ROX.

In an aspect of the present invention, the composition for detecting nucleic acid can attach two or more molecular beacons to graphene oxide at one time. At this time, the composition can attach different fluorescent reagents to the first single strand of the molecular beacon. Preferably, the composition for detecting nucleic acid can attach three molecular beacons to graphene oxide at once, and can attach different fluorescent reagents to the first single strand of the molecular beacon. Herein, the fluorescent reagent can be included in the present invention without limitation as long as it can exhibit fluorescence when the first single strand is dissociated from graphene oxide. For example, the fluorescent reagent can simultaneously include three reagents selected from the group consisting of FAM, Cy5 and ROX.

In an aspect of the present invention, the graphene oxide can be in the form of particles having a size of about 10 nm to about 1 μm, but not always limited thereto. For example, the graphene oxide can be about 10 nm to about 1 μm, about 10 nm to about 700 nm, about 10 nm to about 500 nm, about 10 nm to about 400 nm, about 10 nm to about 300 nm, about 10 nm to about 200 nm, about 10 nm to about 100 nm, about 500 nm to about 1 μm, about 700 nm to about 1 μm, about 200 nm to about 300 nm, or about 400 nm or less, but not always limited thereto.

Since the size of the graphene oxide is small, it can easily pass through the cell membrane and enter into cells together with the second single strand adsorbed on the surface.

In an aspect of the present invention, the graphene oxide can be in the form of a single layer sheet, but not always limited thereto. For example, the graphene oxide in the form of a single layer sheet can absorb a large number of nucleic acid probes in a small amount due to its large surface area at the same mass compared to the graphene oxide not in the form of a single layer sheet.

In an aspect of the present invention, the second single strand can be covalently conjugated to graphene oxide, and specifically, the amine group of the second single strand can be covalently conjugated to the carboxyl group of graphene oxide, but not always limited thereto. When the target nucleic acid is not present, the fluorescent reagent of the first single strand is positioned close to graphene oxide to quench the fluorescence signal. Particularly, the distance between graphene oxide and the fluorescent reagent can be within a sufficient distance that the fluorescent signal is quenched. For example, graphene oxide and the fluorescent reagent can be present within a distance of 3 nm to 5 nm. On the other hand, since the first single strand does not form a covalent bond with graphene oxide, it can be completely separated from the second single strand and graphene oxide by complementary binding to the target nucleic acid, thereby a fluorescence signal can be recovered. Unless the first single strand and the second single strand are sequence-specifically separated, the first single strand is not separated from graphene oxide, so a non-specific signal may not appear.

In an aspect of the present invention, the target nucleic acid can be present in cells, but not always limited thereto. For example, the cells can include cells cultured fixed to a substrate, cells suspended and cultured in a medium, cells in vivo, cells isolated from a living body, or cells treated for analysis, but not always limited thereto. For example, the cells can include living cells or dead cells, and can include cells fixed by a fixing solution, but not always limited thereto.

The present invention also provides a nucleic acid detection method, wherein the molecular beacon is formed by complementarily conjugating the first single strand containing the target nucleic acid binding sequence and the second single strand bound with graphene oxide at least in part, comprising the following steps:

covalently conjugating LNA-containing molecular beacon and graphene oxide;

obtaining a mixture by mixing the composition for detecting nucleic acid obtained in above step and a sample containing the target nucleic acid; and detecting the target nucleic acid in the mixture.

Hereinafter, the method for detecting nucleic acid will be described in detail step by step.

The step of covalently conjugating LNA-containing molecular beacon and graphene oxide can be understood as a step in which the amine group of the molecular beacon and the carboxyl group of graphene oxide are conjugated through covalent conjugation, but not always limited thereto.

The step of obtaining a mixture by mixing the composition and a sample containing the target nucleic acid can be understood as a step of dissociating the complex from graphene oxide by combining the first single strand of LNA-containing molecular beacon and the target nucleic acid.

Herein, it can be understood that the first single strand is hybridized with a sequence having a sequence complementary to at least a part of the target nucleic acid through TMSD (toehold-mediated strand displacement) reaction, and the hybrid is dissociated from graphene oxide.

The step of detecting the target nucleic acid in the mixture can be understood as a step of detecting a corresponding fluorescence signal with a fluorescence detector by recovering the fluorescence signal of the fluorescent substance attached to the first single strand after the first single strand and the target nucleic acid are combined and dissociated from graphene oxide.

Herein, it can be understood as a step of simultaneously detecting two or more target nucleic acids by sensing two or more fluorescent signals with a fluorescent detector using two or more fluorescent substances.

In an aspect of the present invention, the nucleic acid detection method can further include a step of adding a fluorescent reagent to the composition.

Herein, the fluorescent reagent can be one or more reagents selected from the group consisting of FAM (6-carboxyfluorescein), Texas red, fluorescein, HEX (2',4',5',7'-tetrachloro-6-carboxy-4,7-dichlorofluorescein), fluorescein chlorotriazinyl, rhodamine green, rhodamine red, tetramethylrhodamine, FITC (fluorescein isothiocyanate), Oregon green, alexafluor, JOE (6-Carboxy-4',5'-Dichloro-2',7'-Dimethoxyfluorescein), ROX (6-Carboxyl-X-Rhodamine), TET (Tetrachloro-Fluorescein), TRITC (tetramethylrodamine isothiocyanate), TAMRA (6-carboxytetramethylrhodamine), NED (N-(1-Naphthyl) ethylenediamine), cyanine-based dyes and thiadicarbocyanine. The fluorescent reagent can be included in the present invention without limitation as long as it can exhibit fluorescence when the first single strand is dissociated from graphene oxide. For example, the fluorescent reagent can include one or more reagents selected from the group consisting of FAM, Cy5 and ROX.

On the other hand, in the method for detecting nucleic acid with an amplified detection signal of the present invention, it should be understood that the changes and modifications apparent to those skilled in the art, such as the order of detailed condition steps of each step, are also included in the present invention.

In addition, the present invention provides a kit for detecting nucleic acid containing a composition comprising LNA-containing molecular beacon and graphene oxide, wherein the molecular beacon is formed by complementarily conjugating the first single strand containing the target nucleic acid binding sequence and the second single strand bound with graphene oxide at least in part, and the first single strand is separated from the second single strand and bound to the target nucleic acid in the presence of the target nucleic acid.

In an aspect of the present invention, the kit can attach a fluorescent reagent to the first single strand of the molecular beacon. Herein, the fluorescent reagent can be one or more reagents selected from the group consisting of FAM (6-carboxyfluorescein), Texas red, fluorescein, HEX (2',4',5',7'-tetrachloro-6-carboxy-4,7-dichlorofluorescein), fluorescein chlorotriazinyl, rhodamine green, rhodamine red, tetramethylrhodamine, FITC (fluorescein isothiocyanate), Oregon green, alexafluor, JOE (6-Carboxy-4',5'-Dichloro-2',7'-Dimethoxyfluorescein), ROX (6-Carboxyl-X-Rhodamine), TET (Tetrachloro-Fluorescein), TRITC (tetramethylrodamineisothiocyanate), TAMRA (6-carboxytetramethyl-rhodamine), NED (N-(1-Naphthyl) ethylenediamine), cyanine-based dyes and thiadicarbocyanine. Herein, the fluorescent reagent can be included in the present invention without limitation as long as it can exhibit fluorescence when the first single strand is dissociated from graphene oxide. For example, the fluorescent reagent can include one or more reagents selected from the group consisting of FAM, Cy5 and ROX.

Figure 4A:
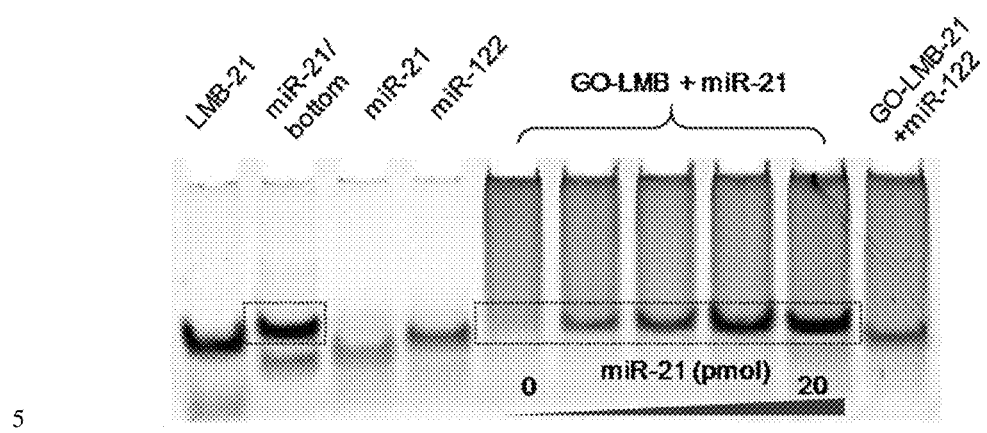
FIG. 4A and FIG. 4B is a set of diagrams showing that the GO-LMB-21 reacts chemically with a target (miR-21) and that the signal intensity of gel electrophoresis is increased in proportion to the concentration of the target (miR-21).
Figure 4B:
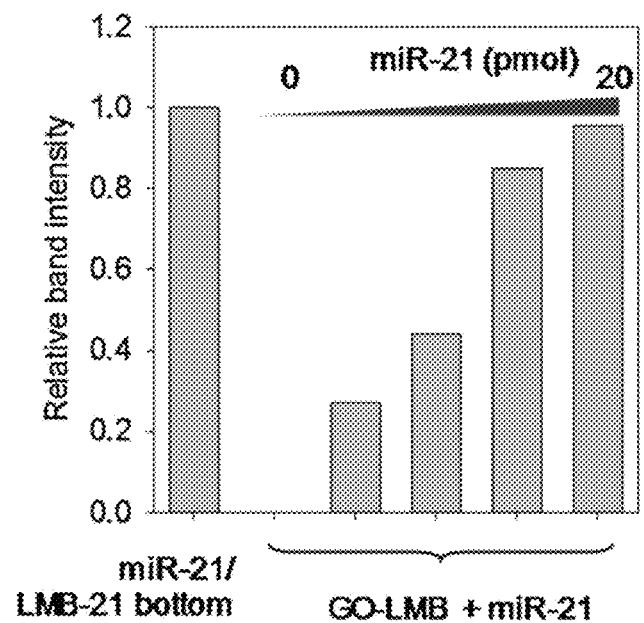
Figure 5A:
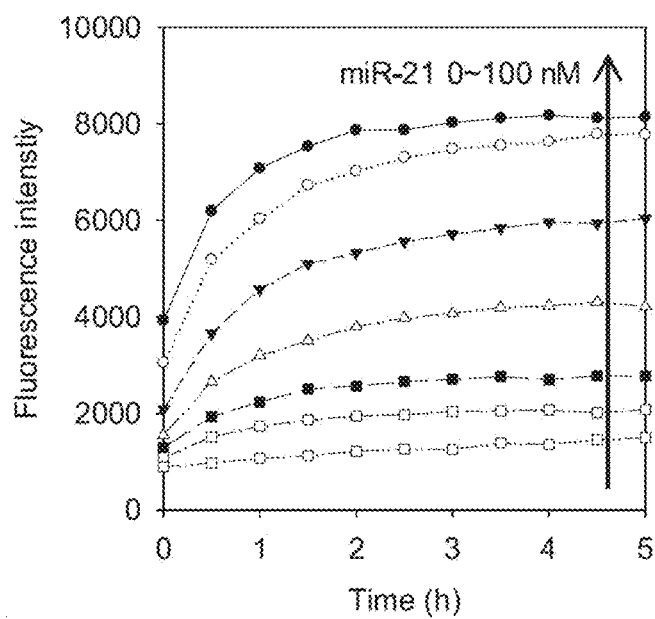
FIGS. 5A, 5B, 5C, and 5D is a set of graphs showing the intensity of the fluorescent signal according to the concentration of the target (miR-21) used in the embodiments of the present invention.
Figure 5B:
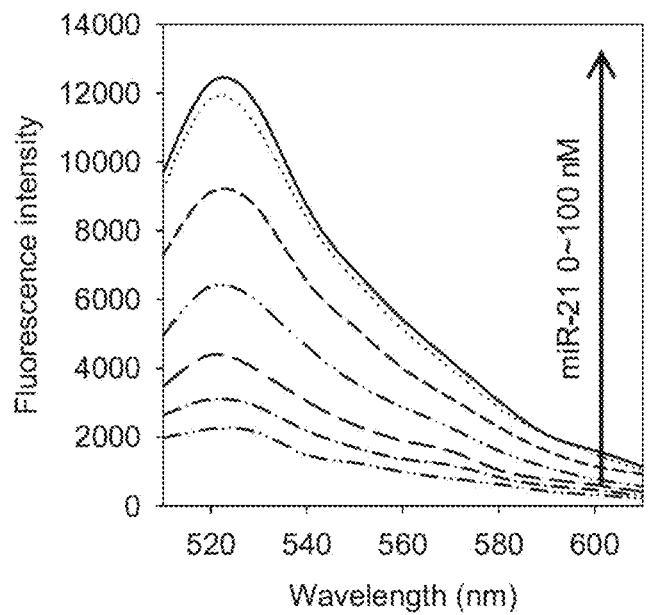

According to the composition, kit and method for detecting nucleic acid, the first single strand of LNA-containing molecular beacon complementarily bound to the second single strand, and in the process, the fluorescent reagent attached to the first single strand was quenched. The toehold region of the first single strand containing LNA and the target nucleic acid formed a complex through TMSD (toehold-mediated strand displacement) reaction (see FIGS. 1 and 2), and the complex was separated from the second single strand of the molecular beacon and graphene oxide, so that the fluorescence signal quenched by graphene oxide was recovered. A stronger fluorescent signal appeared in proportion to the concentration of the target nucleic acid (see FIGS. 4A and 4B), and the intensity of the fluorescent signal was increased over time, but the fluorescent signal was stabilized after a certain time (FIGS. 5A and 5B). Due to the strong binding force of LNA in the toehold region, it was possible to specifically detect only the target nucleic acid (see FIGS. 5C and 5D), and to accurately detect the target nucleic acid at a very low concentration of pM level with high sensitivity (see FIGS. 6A and 6B). Compared to the conventional GO-based sensor, it was confirmed that the sensor of the present invention showed much higher detection ability (see FIGS. 7A, 7B and 7C) and did not lower the high specificity and sensitivity described above in cell lysates (see FIGS. 8A, 8B and 8C).

Figure 10A:
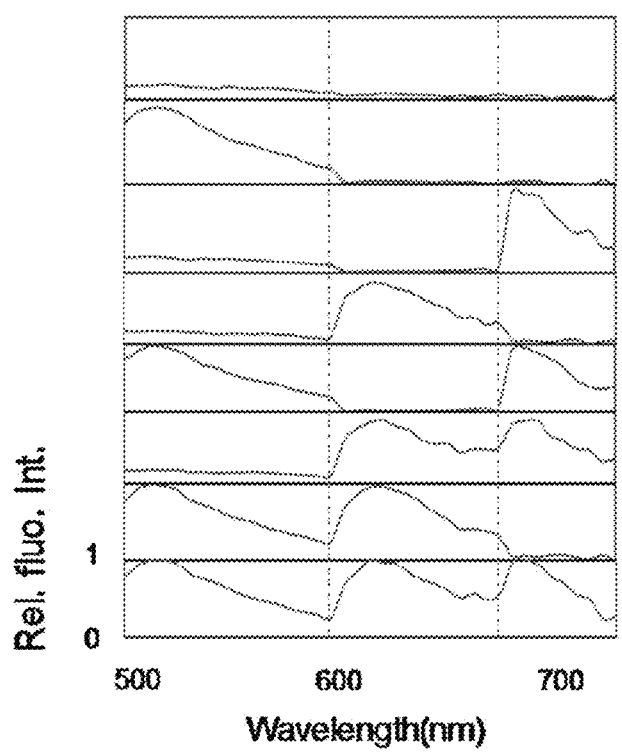
FIG. 10A, FIG. 10B and FIG. 10C is a set of diagrams showing the experimental results of simultaneously detecting multiple target nucleic acids by diversifying the wavelength of a fluorescent signal.
Figure 10B:
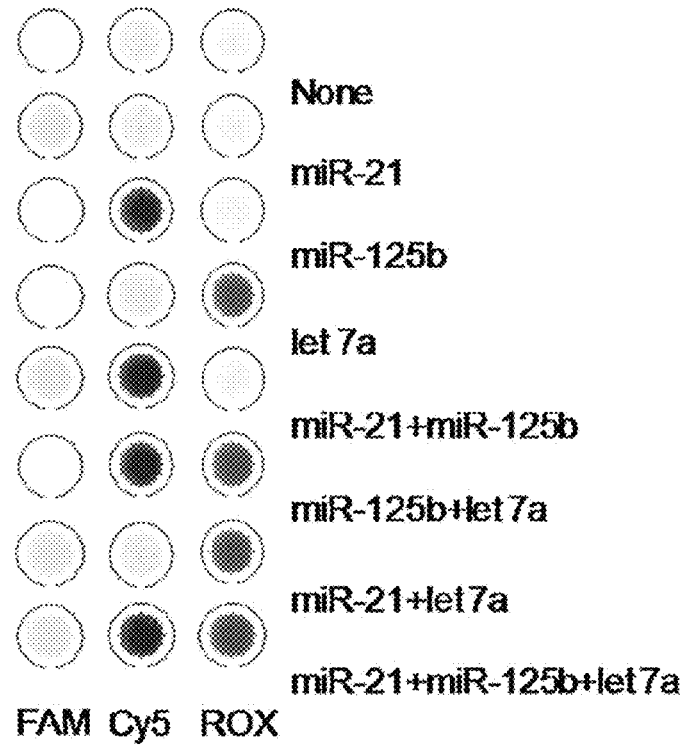
Figure 10C:
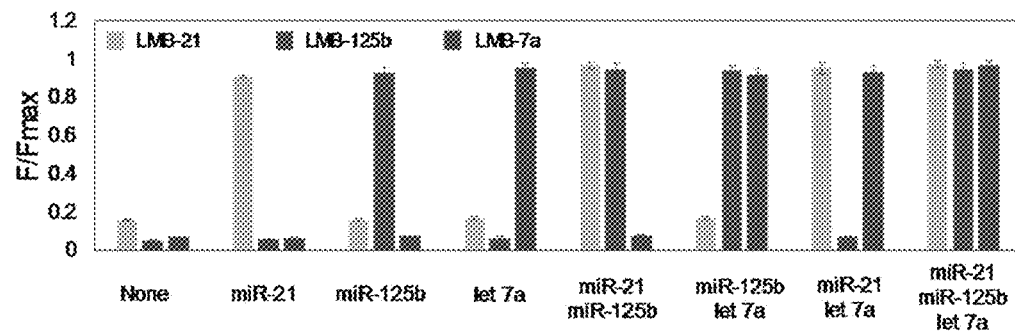

In addition, multiple target nucleic acids can be detected simultaneously by conjugating different types of duplex molecular beacons that detect different types of nucleic acids to one graphene oxide and attaching different fluorescent reagents to each molecular beacon to diversify the fluorescence signal (see FIGS. 10A, 10B and 10C). Through the present invention, it is possible to easily and accurately detect a nucleic acid biomarker whose expression level is specifically changed according to toxic diseases and disease progression. By applying the nanosensor of the present invention to a non-clinical study and applying it to the toxicity evaluation through miRNA, a synergy effect with existing research can be achieved.

EXAMPLES

Hereinafter, the present invention will be described in detail by the following examples.

However, the following examples are only for illustrating the present invention, and the contents of the present invention are not limited thereto.

Example 1: Preparation of Target Nucleic Acid Detection System

Figure 3:
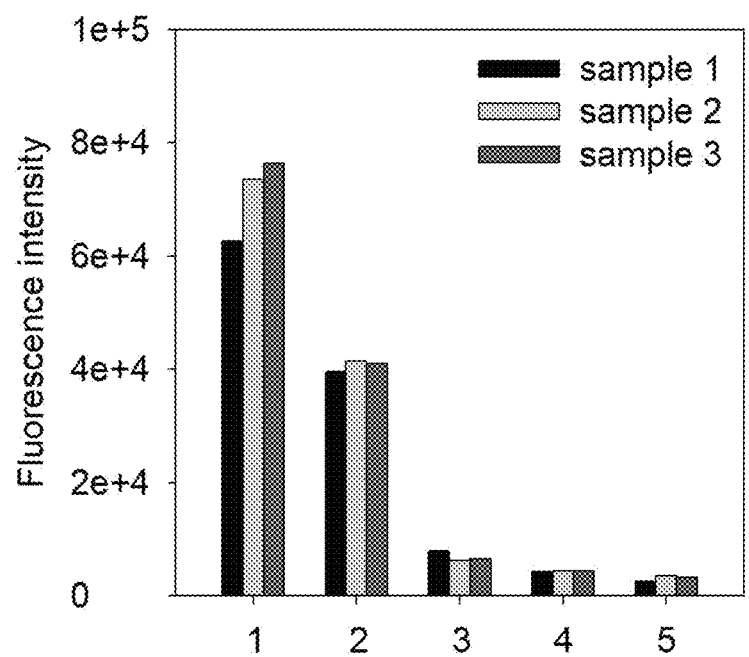
FIG. 3 is a graph showing the intensity of the fluorescence signal according to the number of washings when the mixture of LMB and GO is washed with 1×PBS and 0.02% HSD solution.

To prepare the LNA-containing molecular beacon (LMB) as the target nucleic acid detection system, 100 μM of the amine-functionalized upper strand DNA (10 μL) was mixed with an equal amount of the FAM-labeled bottom strand DNA in 1×PBS (phosphate-buffered saline). Then, the mixture was annealed by heating at 90° C. for 5 minutes, followed by slow cooling to room temperature for 1 hour. For the conjugation of LMB and graphene oxide, 500 pmol of the annealed LMB was mixed with 100 μg of carboxylated graphene oxide (GO, Sigma-Aldrich, USA) in 1×PBS (pH 7.2, NaCl 137 mM and KCl 2.7 mM) containing 10 mM 1-ethyl-3-(3-dimethylaminopropyl)carbodiimide (EDC, Sigma-Aldrich, USA). The mixture was shaken at room temperature for 3 hours, followed by washing with 1×PBS and 0.02% herring sperm DNA (HSD, Sigma-Aldrich, USA) solutions. The washing procedure was repeated 5 times, and each supernatant was confirmed by measuring the fluorescence intensity at ex480/em520 nm (FIG. 3). The resulting purified GO-LMB-21 complex was stored at 4° C. As a target miRNA, miR-21 was selected because of its strong association with cancer (Table 1), and a thermocycler (Bio-Rad, USA) was used for temperature control.

TABLE 1

Double-stranded nucleotide sequences of miR-21 and LMB-21

| Nucleic acid strand | | Sequence (5'→3') |
|---|---|---|
| Target RNA | miR-21 | U AGC UUA UCA GAC UGA UGU UGA |
| LMB-21 | Upper strand | TCA GAC TGA TGT TGA-NH$_2$ |
| | Bottom strand | FAM-TCA ACA TCA GTC TGA TAA GCT A |

RNA strands were purchased from Bioneer (Daejon, Korea). Amine-functionalized DNA strands were purchased from Genotech (Daejon, Korea), and LNA-embedded DNA strands were purchased from Integrated DNA Technologies (IA, USA).

Particularly, the LMB-21 probe was composed of a FAM-labeled bottom strand, which possessed a complementary sequence for miR-21 and an amine-terminated upper strand, which was 7-nt shorter than the bottom strand (FIG. 2). In the 7-nt toehold region, a single thymine LNA was incorporated to enhance the binding affinity for the target miRNA. The GO and LMB conjugate for miR-21 (GO-LMB-21) was prepared by conjugating the amine-functionalized LMB-21 with the carboxylated GO using EDC coupling chemistry.

Experimental Example 1: Confirmation of Activation of Target Nucleic Acid Detection System by Target miRNA It was confirmed by polyacrylamide gel electrophoresis that the target nucleic acid detection system comprising LNA-containing molecular beacon and graphene oxide of the present invention was activated by the target miRNA.

Particularly, 10 pmol of LMB-21, 10 pmol of miR-21/LMB-21_B, 20 pmol of LMB-21 and 20 pmol of miR-122 were added to the lanes 1 to 4 of 18% native polyacrylamide gel, respectively, 5 μg of GO-LMB-21 and miR-21 (0, 2.5, 5, 10 and 20 pmol) were added to the lanes of 5 to 9, respectively, and 5 μg of GO-LMB-21 and 20 pmol of miR-122 were added to the lane 10, followed by electrophoresis.

As a result, upon mixing with miR-21, the GO-LMB-21 showed a single band, whereas the GO-LMB-21 without miR-21 did not display the band (FIG. 3A). These results indicated that the LMB-21 was chemically attached on the GO surface and that miR-21 successfully induced the TMSD reaction in GO-LMB-21 to form the miR-21/bottom duplex.

The results of the lanes 6 to 9 (5 μg of GO-LMB-21 and miR-21 (0, 2.5, 5, 10 and 20 pmol)) of polyacrylamide gel electrophoresis were analyzed in comparison to that of the lane 2 (miR-21/LMB-21_B 10 pmol). As a result, the gel electrophoresis band intensity was increased in proportion to the concentration of miR-21. These results indicated that the formation of the miR-21/bottom duplex was increased in proportion to the concentration of miR-21 (FIG. 4B).

Experimental Example 2: Analysis of Fluorescence Signal of Target Nucleic Acid Detection System According to Target miRNA Concentration In order to supplement the results of Experimental Example 1 in which the detection performance of the nucleic acid detection system comprising LNA-containing molecular beacon and graphene oxide of the present invention was increased in proportion to the concentration of the target miRNA, the fluorescent signal of the target nucleic acid detection system according to the concentration of the target miRNA was analyzed.

A 12.5 μg/ml solution of GO-LMB-21 was prepared in 1×PBS and was mixed with a broad range of concentrations (0-100 nM) of miR-21. The fluorescence intensity of the Fluorescein (FAM), labeled at the bottom strand of LMB-21, was quenched by FRET. The fluorescence signal was measured using a multi-mode microplate reader (Biotek, USA) at ex 480/em 520 nm.

As a result, upon addition of miR-21, the newly formed FAM-labeled bottom/miR-21 duplex was released, and the fluorescence intensity was recovered gradually. The fluorescence intensity was increased according to the increase in the concentration of miR-21 and stabilized after 2 hours (FIG. 5A). In addition, the fluorescence signal intensity according to the concentration of miR-21 in the effective fluorescence wavelength control region of FAM was analyzed. As a result, the fluorescent signal intensity was increased in proportion to the concentration of miR-21 at 520 nm (FIG. 5B). These results indicated that the fluorescence signal intensity of the target nucleic acid detection system was increased according to the increase in the concentration of the target miRNA.

Experimental Example 3: Confirmation of Specificity of Target Nucleic Acid Detection System To confirm the sequence specificity of the target nucleic acid detection system to the target miRNA, nucleic acid detection using other miRNA families, including the target miRNA, was performed in a solution.

Particularly, the fluorescence signal of the target nucleic acid detection system was analyzed in the same manner as described in Experimental Example 2 except that miR-122, let 7a and scrambled RNA (scRNA) were mixed with GO-LMB-21.

Figure 5C:
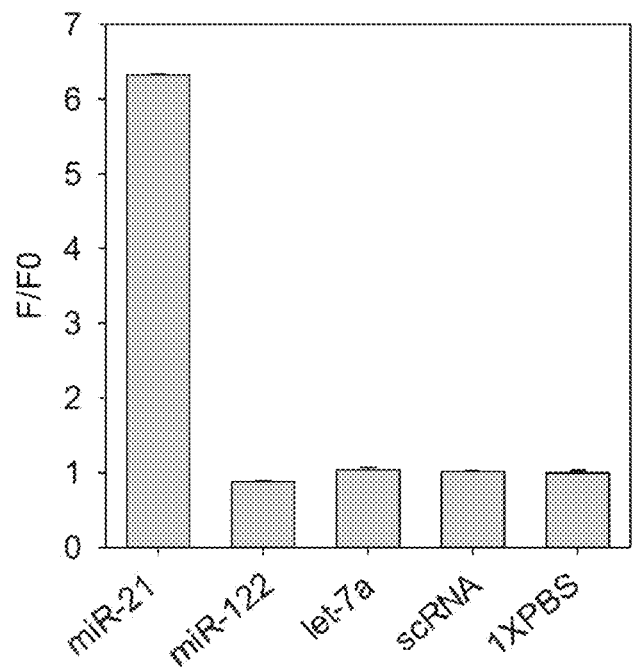
Figure 5D:
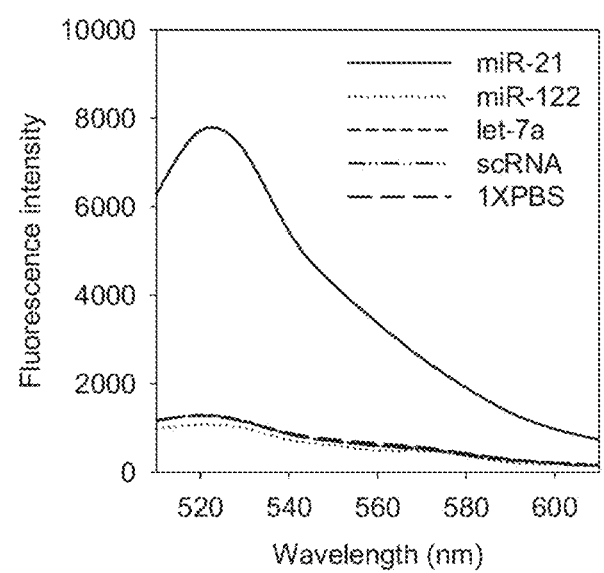

As a result, miR-21 induced a remarkable increase in the fluorescence of GO-LMB-21, whereas miRNAs of other families showed little changes in the fluorescence intensity, which was similar to that of the negative control (FIG. 5C). In addition, the fluorescence signal intensity in the effective fluorescence wavelength control region of FAM was analyzed. As a result, the fluorescence signal intensity of GO-LMB-21 was increased by miR-21 at 520 nm, but miRNAs of other families did not affect the fluorescence signal of GO-LMB-21 (FIG. 5D). These results indicated that the GO-LMB-21 recognized the target miRNA sequence specifically and produced a quantitative fluorescence signal with enhanced sensitivity in 2 hours, which corresponded to the target miRNA concentration.

Experimental Example 4: Confirmation of Sensitivity of Target Nucleic Acid Detection System To confirm the sensitivity of the target nucleic acid detection system comprising LNA-containing molecular beacon and graphene oxide of the present invention and the existing GO-based miRNA detection system, the fluorescence signal intensity of each system was analyzed.

Particularly, various concentrations of miR-21, ranging from 0 to 100 nM, were mixed with a 12.5 jig/ml solution of GO-LMB-21. In addition, the same experiment was repeated using GO-MB-21, which does not have LNA in the toehold region, to analyze the limit of detection (LOD) in each case.

Figure 6A:
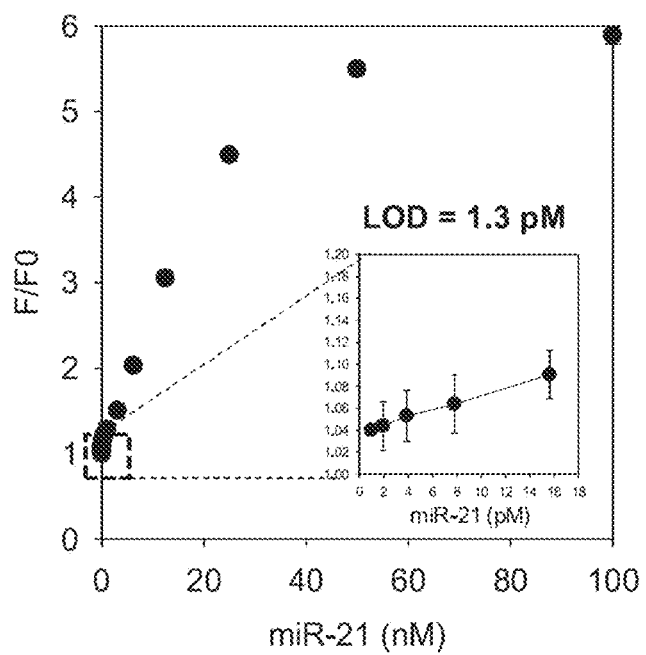
FIG. 6A and FIG. 6B is a set of graphs showing the detection limits of GO-LMB compared to GO-MB.

As a result, GO-LMB-21 showed a linear increase in the fluorescence between 0 and 25 nM, and the detection limit was determined to be 1.3 pM according to the equation, LOD=3.3 (SD/S) (FIG. 6A).

SD=standard deviation, S=slope.

Figure 6B:
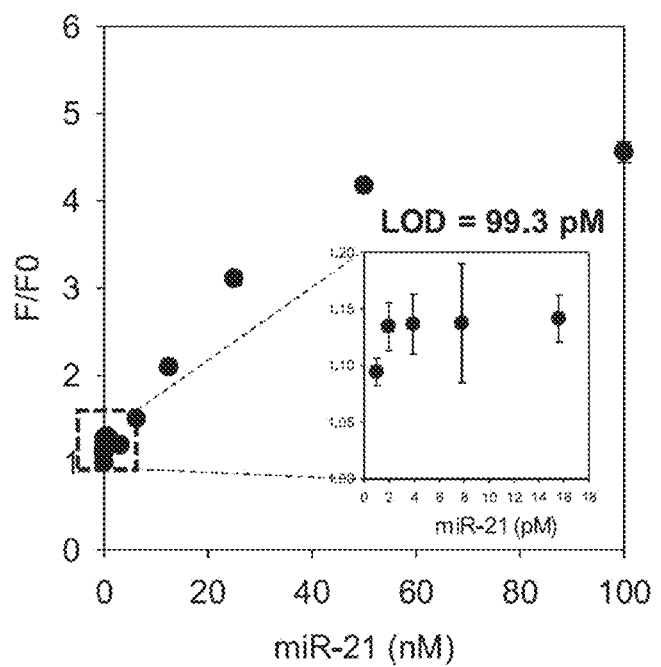

While GO-MB-21 also exhibited a time-dependent increase of the fluorescence signal intensity and demonstrated high selectivity in the presence of miR-21, the rate of increase of the fluorescence signal intensity was much slower than that of GO-LMB-21. With varied concentrations of miR-21, which ranged from 0 to 100 nM, GO-MB-21 exhibited smaller increases in fluorescence intensity and indicated a LOD of 99.3 pM (FIG. 6B). Therefore, the LOD of the target nucleic acid detection system of the present invention was much lower than that of the conventional GO-based miRNA detection system, which indicated that the incorporation of LNA in the toehold region overwhelmingly helped strengthen the binding affinity with the target and contributed to enhance sensitivity Apart from the above experiment, the fluorescence signal intensity of GO-LMB and the conventional GO sensor was analyzed to confirm the detection sensitivity of the GO-LMB of the present invention compared to that of the conventional ssDNA conjugated GO sensor.

Particularly, the fluorescence signal intensity when the concentration of miR-21 was 0 or 100 nM was compared using GO-LMB-21 and GO-cDNA-21 with miR-21 as the target miRNA.

Figure 7A:
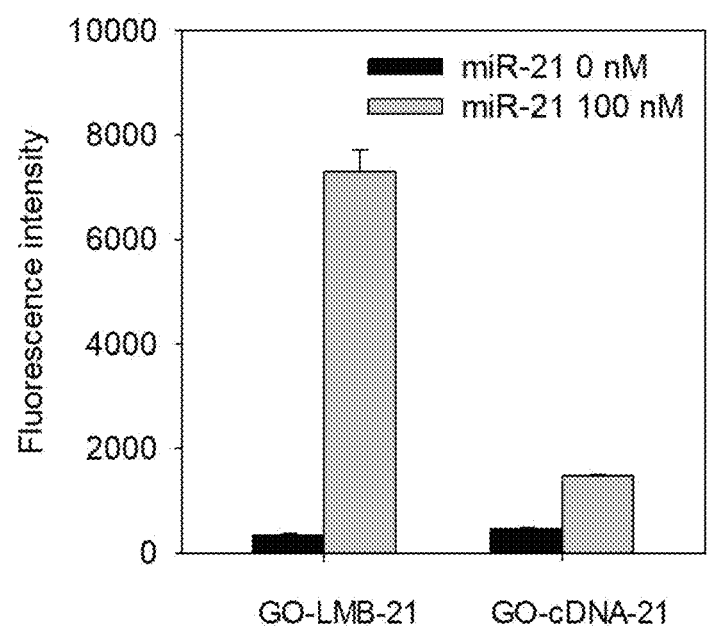
FIG. 7A, FIG. 7B, FIG. 7C, and FIG. 7D is a set of graphs showing the intensity of the fluorescent signal of LNA-containing GO-LMB-21 and GO-cDNA-21 using a single strand in the presence of miR-21.
Figure 7B:
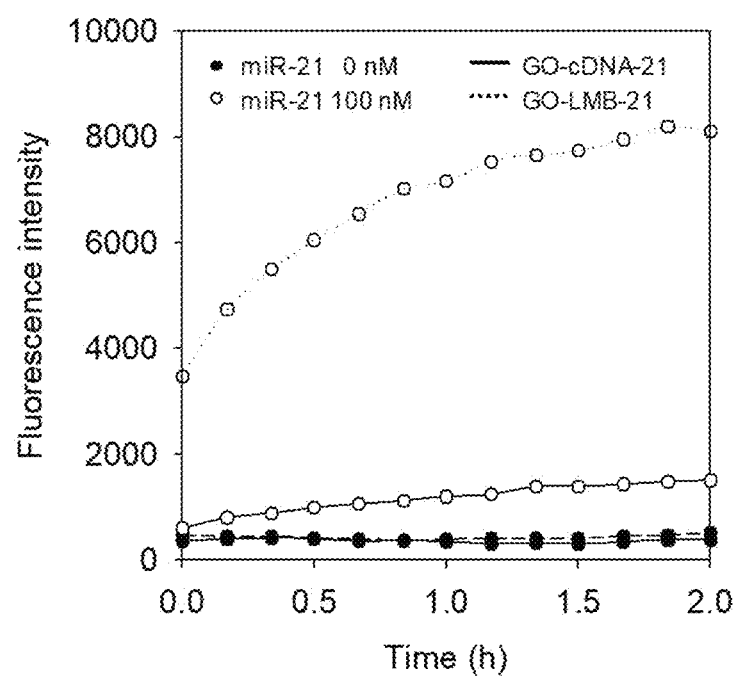
Figure 7C:
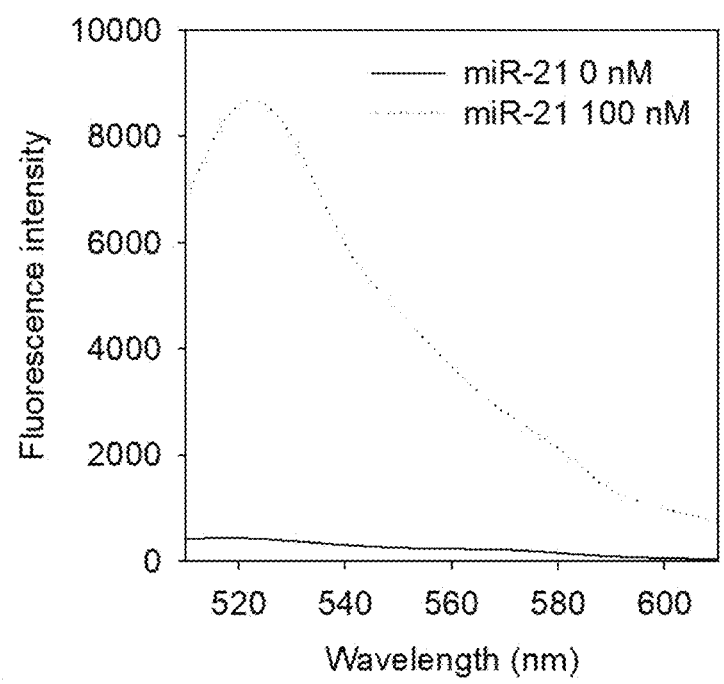
Figure 7D:
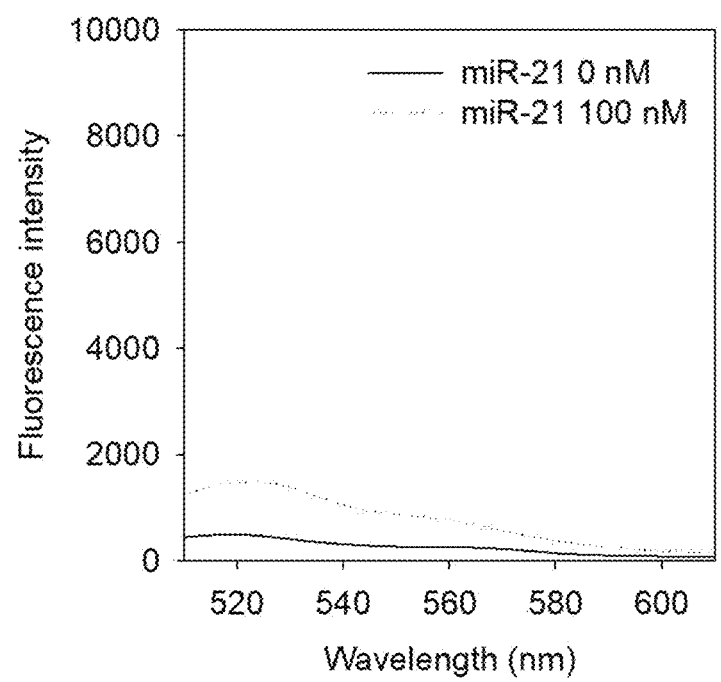

As a result, when the concentration of miR-21 was 100 nM, the fluorescence signal intensity of GO-LMB-21 was much higher than that of GO-cDNA-21 (FIGS. 7A, 7C and 7D). GO-LMB-21 also exhibited higher fluorescence signal intensity over time (FIG. 7B). These results indicated that the GO sensor using a duplex comprising the first single strand attached with a fluorescent reagent and the second single strand covalently conjugating to GO had a higher sensitivity than the conventional single-stranded GO sensor.

Figure 8A:
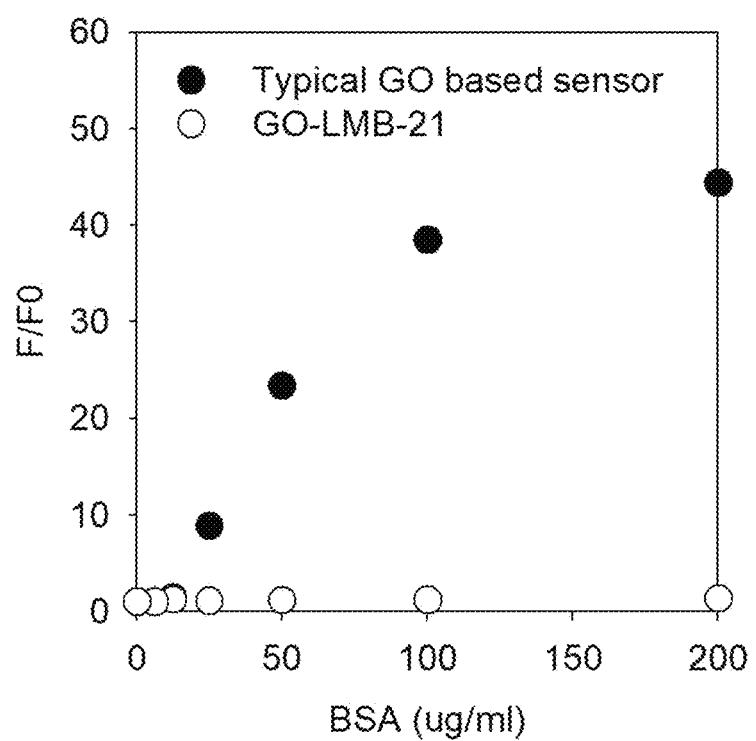
Figure 8B:
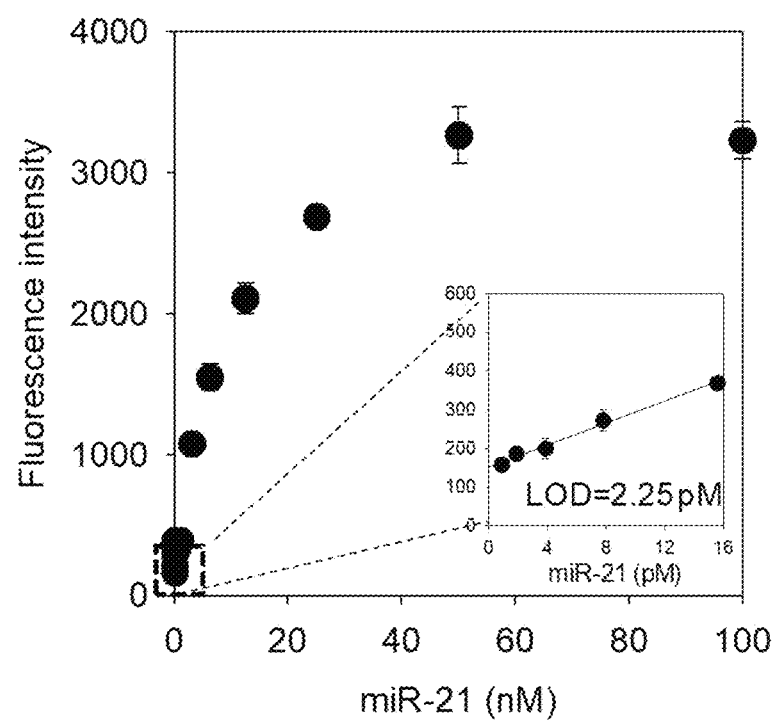
Figure 8C:
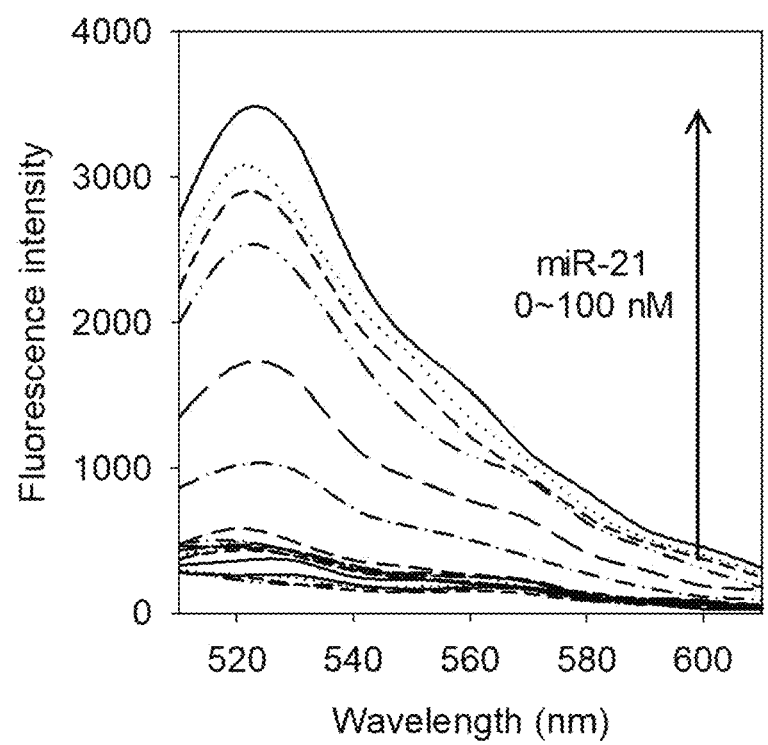

Experimental Example 5: Confirmation of Target Nucleic Acid Detection System Activation in Cell Lysate The fluorescence signal intensity was analyzed to confirm that the target nucleic acid detection system comprising LNA-containing molecular beacon and graphene oxide of the present invention can detect the target miRNA even in a biological sample by mixing with bovine serum albumin (BSA, Sigma-Aldrich, USA).

with a comparable LOD of 2.25 pM in the presence of 100 µg/ml of BSA (FIGS. 8B and 8C). This low LOD demonstrated that GO-LMB could maintain the sensing capability even in protein-rich samples without appreciable loss of sensing performance.

Figure 9:
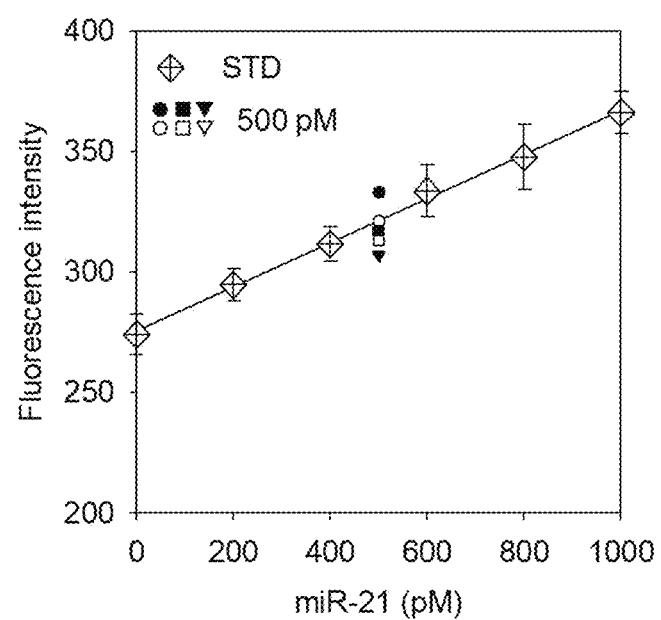
FIG. 9 is a linear standard curve showing the intensity of the fluorescence signal of the spiked miR-21 according to the concentration in HepG2 cell lysate (10,000 cells/well).

To confirm the accuracy of such experiments in real samples, the present inventors additionally performed the quantification of spiked miR-21 in a HepG2 lysate (10,000 cells/well). As a result, a standard curve was derived from a series of spiked miR-21 concentration (0-1 nM)). In addition, upon the separate addition of 500 pM of spiked miR-21 to the system, the obtained fluorescence intensities were found to be in good agreement with the estimated values from the standard curve (FIG. 9).

Experimental Example 6: Confirmation of Multi-Target Nucleic Acid Detection of Target Nucleic Acid Detection System Through Diversification of Fluorescence Signal In order to confirm that multiple targets can be simultaneously detected through the target nucleic acid detection system of the present invention, a detection experiment was performed using various fluorescent materials.

Particularly, miR-21, miR-125b, and let-7a, which are the representative miRNA biomarkers for breast cancer, were selected for the experiment (Table 2). The LMB probe targeting miR-21 was labeled with FAM, the LMB probe targeting miR-125b was labeled with cyanine 5 (Cy5), and the LMB probe targeting let-7a was labeled with 6-carboxylxrhodamine (ROX). They showed emission maxima at 520 (green), 665 nm (red), and 605 (orange), respectively, with excitations at 480, 619, and 564 nm, respectively. The multiplex sensor, termed GO-LMB-21/125b/7a, was prepared by conjugating GO with the three kinds of LMBs, which were FAM-LMB-21, Cy5-LMB-125b, and ROX-LMB-7a, followed by purification of the conjugates with HSD solution. For multiplex detection, GO-LMB-21/125b/7a was simply mixed with each target miRNA (100 nM) or various combinations of target miRNAs.

TABLE 2

Nucleotide sequences of LMB-125b and LMB-let 7a duplexes and target RNA

| | Nucleic acid strand | Sequence (5'→3') |
|---|---|---|
| Target RNA | miR-125b | UCC CUG AGA CCC UAA CUU GUG A |
| | let-7a | UGA GGU AGU AGG UUG UAU AGU U |
| | miR-122 | UGG AGU GUG ACA AUG GUG UUU G |
| | scRNA | GCA UCG AGC UGA AGG GCA UCG ACU UCA |
| LMB-125b | Upper strand | GA CCC TAA CTT GTG A-NH$_2$ |
| | Bottom strand | Cy5-TCA CAA GTT AGG GTC TCA GGG A |
| LMB-let 7a | Upper strand | GT AGG TTG TAT AGT T-NH$_2$ |
| | Bottom strand | ROX-ACC TAT ACA ACC TAC TAC CTC A |

As a result, in the case of the conventional GO sensor using a cDNA probe, the fluorescence signal was gradually increased with the increase in the concentration of BSA due to the competitive interaction of BSA and cDNA with GO. However, the covalently conjugated GO-LMB sensor showed little change in fluorescence response in biological samples (FIG. 8A).

Next, the present inventors carried out the LOD test with miR-21 spiked in protein-rich samples. As a result, GO-LMB-21 showed a quantitative fluorescence intensity increase according to the increase in miR-21 concentration As a result, the green, red, and orange fluorescence emission spectra emitted by TSMD reaction with each target miRNA and images were obtained only in the samples containing each of the corresponding miRNA targets (FIGS. 10A, 10B and 10C).

From the above results, it was confirmed that the target nucleic acid detection system of the present invention can detect multiple target nucleic acids simultaneously because it uses multiple fluorescent signals and there is no interference between the signals, so it can be effectively used for the diagnosis of miRNA-based diseases.

What is claimed is:

1. A method for detecting a target nucleic acid comprising:
   (a) mixing a molecular beacon containing locked nucleic acid (LNA) and a sample containing the target nucleic acid to form a composition, wherein the molecular beacon containing LNA is a double-stranded nucleic acid complex comprising a first single strand comprising a toehold region complementary to the target nucleic acid and a fluorescent reagent, and a second single strand bound with graphene oxide, wherein the first single strand and the second single strand are complementary to each other at least in part;
   (b) complementarily binding the toehold region of the first single strand to the target nucleic acid and displacing the second single strand through toehold-mediated strand displacement; and
   (c) detecting a fluorescence signal of the fluorescent reagent, thereby detecting the target nucleic acid.

2. The method according to claim 1, wherein the graphene oxide is in the form of particles having a size of 10 nm to 1 µm.

3. The method according to claim 1, wherein the fluorescent reagent is selected from the group consisting of FAM (6-carboxyfluorescein), Texas red, fluorescein, HEX (2',4', 5',7'-tetrachloro-6-carboxy-4, 7-dichlorofluorescein), fluorescein chlorotriazinyl, rhodamine green, rhodamine red, tetramethylrhodamine, FITC (fluorescein isothiocyanate), Oregon green, alexafluor, JOE (6-Carboxy-4',5'-Dichloro-2', 7'-Dimethoxyfluorescein), ROX (6- Carboxyl-X-Rhodamine), TET (Tetrachloro-Fluorescein), TRITC (tetramethylrodamine isothiocyanate), TAMRA (6-carboxytetramethyl-rhodamine), NED (N-(1-Naphthyl) ethylenediamine), cyanine-based dyes, thiadicarbocyanine, and a mixture thereof.

4. The method according to claim 1, wherein two or more molecular beacons are attached to the graphene oxide and each molecular beacon comprises a different fluorescent reagent.

5. The method according to claim 1, wherein the second single strand of the molecular beacon containing LNA is covalently conjugated to the graphene oxide.

6. The method according to claim 5, wherein an amine group of the second single strand of the molecular beacon containing LNA is covalently conjugated to a carboxyl group of the graphene oxide.

7. The method according to claim 6, wherein the fluorescent reagent is attached to a 5' end of the first single strand.

8. The method according to claim 1, wherein the fluorescent reagent is positioned 3 to 5 nm from the graphene oxide in the composition of step (a).

9. The method according to claim 1, wherein the target nucleic acid includes DNA or RNA.

10. The method according to claim 1, wherein the graphene oxide is in the form of particles having a size of 10 nm to 200 nm.

11. The method according to claim 1, wherein the target nucleic acid is detected in a cell lysate.

* * * * *